United States Patent [19]

Middaugh

[11] 4,242,311

[45] Dec. 30, 1980

[54] GARBAGE AND TRASH CONTAINER SELECT SPRAY SYSTEM

[76] Inventor: Ralph E. Middaugh, 144 Holiday Dr., Martinez, Ga. 30907

[21] Appl. No.: 18,498

[22] Filed: Mar. 8, 1979

[51] Int. Cl.³ .......................... B08B 3/10; A61L 2/18; A61L 11/00; B08B 9/00

[52] U.S. Cl. ............................... 422/302; 134/167 R; 134/172; 422/5

[58] Field of Search ............................ 422/5, 28, 302; 239/172; 134/167 R, 172, 174

[56] References Cited

U.S. PATENT DOCUMENTS

| | | | |
|---|---|---|---|
| 2,764,171 | 9/1956 | Nolte | 134/145 |
| 2,951,490 | 9/1960 | Cullier | 134/107 |
| 3,207,166 | 9/1965 | Wintzer | 134/115 R |
| 3,212,511 | 10/1965 | Cullier | 134/107 |
| 3,219,275 | 11/1965 | Green | 239/172 |
| 3,291,144 | 12/1966 | Diamond | 134/104 |
| 3,324,866 | 6/1967 | Davis | 134/52 |
| 3,338,438 | 8/1967 | Holtkamp | 414/408 |
| 3,372,875 | 3/1968 | Torrey | 239/129 |
| 3,881,950 | 5/1975 | Pettit | 134/115 R |
| 3,901,255 | 8/1975 | Pettit | 134/107 |

*Primary Examiner*—Barry S. Richman
*Attorney, Agent, or Firm*—Jones, Tullar & Cooper

[57] ABSTRACT

A system for selectively spraying a treating material such as an insecticide and/or odor suppressor into the interior of a commercial garbage or trash container. The system includes a suitable spray nozzle assembly carried on the cross bar of the lifting frame of a conventional front loading sanitation truck and a biased access door in the trash container or bin through which a spray nozzle may be inserted into the interior of the container. A container of the insecticide and/or odor suppressor is carried on the truck together with controls placed in the vehicle's cab and controlled by the operator to insert the spray nozzle into the container, spray the container's interior, and retract the spray nozzle.

6 Claims, 4 Drawing Figures

Fig. 1
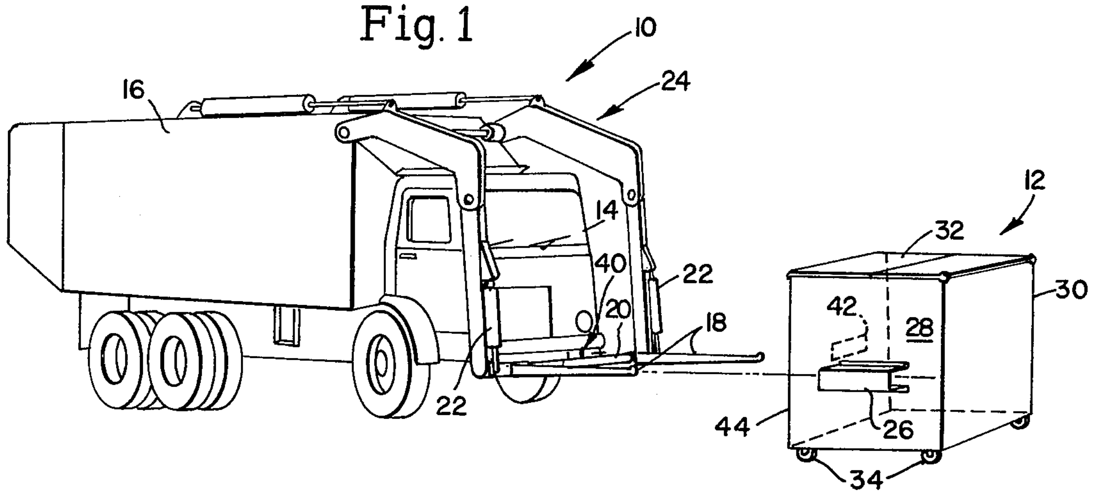
Fig. 2
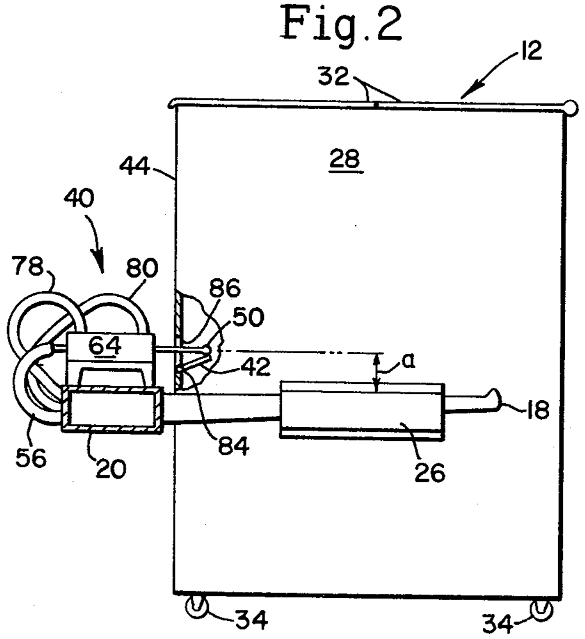
Fig. 3
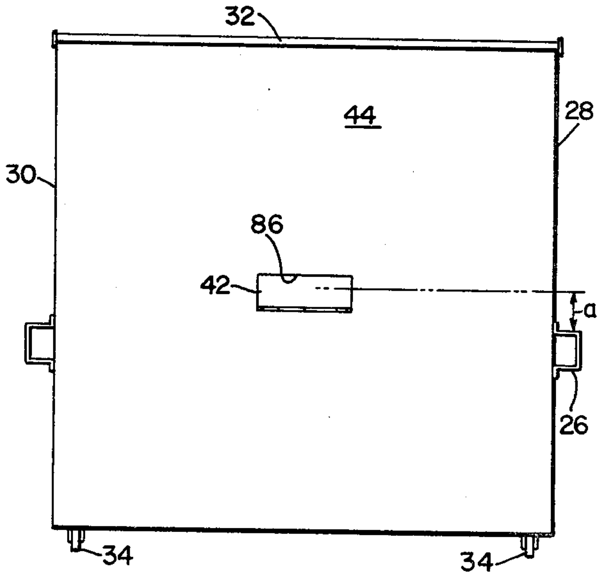
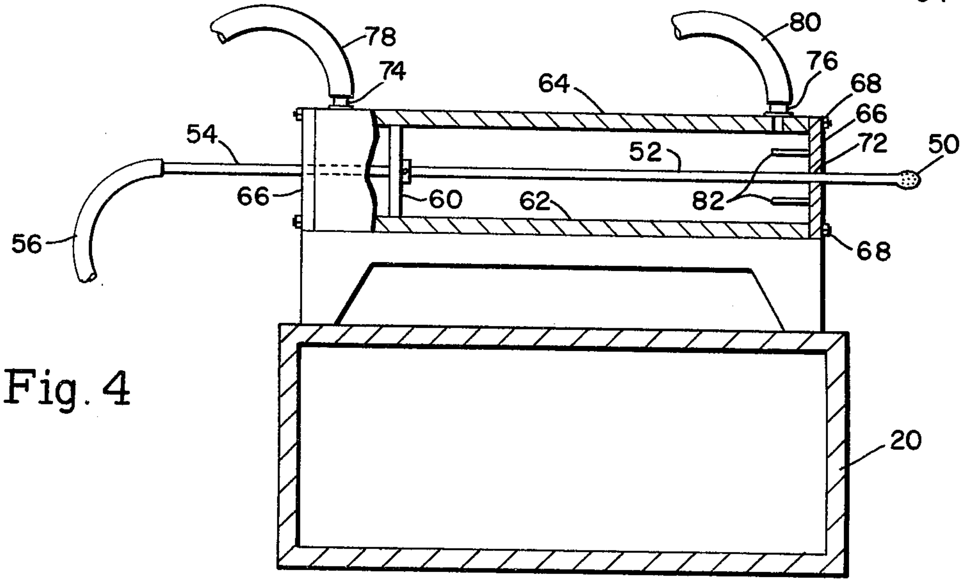
Fig. 4

GARBAGE AND TRASH CONTAINER SELECT SPRAY SYSTEM

FIELD OF THE INVENTION

The present invention is directed generally to a garbage and trash container spray system. More particularly, the present invention is directed to a container spray system for selectively spraying a treating material such as an insecticide and/or odor suppressor into a commercial trash container. Most specifically, the present invention is directed to a select spray system carried by a front loading trash truck and controlled by the truck operator from within the cab of the truck.

A commercial trash or garbage bin is modified by placing a biased access door in a wall portion of the container between the pickup sleeves. The cross bar of the lifting assembly of a front loading trash truck carries a movable spray nozzle assembly which is under the control of the truck operator. A spray nozzle can be inserted through the access door into the container and the insecticide/odor suppressor sprayed into the interior of the container. A supply source of the insecticide or disinfectant is carried on the truck together with suitable hydraulic, or pneumatic, means to insert and retract the spray nozzle and to deliver the treating material to the spray nozzle.

DESCRIPTION OF THE PRIOR ART

The use of large bins or containers for the deposit of trash and/or garbage from commercial establishments and residential apartments has grown substantially. These trash or garbage bins or containers are usually emptied periodically by a front loading dump truck which carries a pair of forwardly extending lift forks that are insertable into pickup sleeves placed on opposed sides of the containers so that the container can be lifted off the ground and its contents dumped into the body of the truck. Since these containers are quite large, they may not be emptied for a substantial period of time such as a week or more in some instances. Because these containers often receive garbage as well as trash, many municipalities have required that the interior of the container be treated periodically with a treating material such as a disinfectant and/or odor suppressor. Even when not required by statute, such treatment of the containers is a desirable service which users of the containers may request from the company which supplies and services the containers.

Most front loading containers are presently sprayed by the driver of the truck who, after the trash or garbage has been emptied, must leave the cab of the truck, unwind a hose attached to a spray tank of insecticide and/or odor suppressor, spray the interior of the container, rewind the hose, and return to the cab of the truck. A suitable spray tank and hose arrangement for performing this task is shown in U.S. Pat. No. 3,372,875 to Torrey. It will be readily apparent that there are a number of drawbacks to the presently available container treatment systems. Since the truck may empty 60 to 100 trash or garbage containers during a single day, the driver must perform this procedure many times. The task soon becomes onerous and often is not performed as thoroughly as it should be. The time involved is also substantial and may consume an additional hour or more which could be spent in servicing other customers. The driver is also subject to repeated exposures to the material being sprayed into the containers and such exposure is at least unpleasant and may be detrimental to the health of the driver. The customer either must have a spray treatment of the trash containers to comply with local statutes or desires this service for reasons of sanitation, but the driver who must perform the service views it as a time consuming, tiresome, disagreeable chore, thus causing a continuous controversy between the customer and the trash container servicing contractor over the performance of the service.

SUMMARY OF THE INVENTION

It is an object of the present invention to provide a select spray system for treating trash or garbage containers with an insecticide and/or odor suppressor.

A further object of the select spray system in accordance with the present invention is to provide a spray system which is controllable from the cab of a trash truck.

Yet another object of the present invention is to provide a spray system which is suitable for use with a variety of sizes of trash or garbage containers.

Still a further object of the select spray system in accordance with the present invention is to provide a spray system which is efficient, durable, and simple to maintain and operate.

As will be discussed in greater detail in the description of a preferred embodiment set forth hereinafter, the garbage and trash container select spray system in accordance with the present invention includes a spray nozzle assembly which is carried on the cross bar of the lifting assembly of a front loading trash truck and a cooperating biased spray access door formed in one of the walls of the container to be sprayed. The system further includes suitable control means in the cab of the truck to optionally insert the spray nozzle into the container, to dispense the spray from a suitable tank, and to retract the spray nozzle from the container.

The select spray system in accordance with the present invention has numerous advantages over the prior procedures discussed previously. Chief among these is that the spraying of the insecticide, odor suppressor or other treating material can be accomplished from the cab of the vehicle without requiring the driver to leave the truck. The spraying is easily accomplished and is done much more effectively and dependably than in the prior system which required the driver to leave the cab of the truck. The spray nozzle is structured to enter the container and to completely spray its interior. This results in more uniform conformance to statutes and/or customer wishes and creates a better business relationship. The driver of the truck is no longer brought into contact with the insecticide or odor suppressor which may be harmful to his health.

The driver is not required to leave the truck, and the spray application is performed much more rapidly than in prior systems thereby providing additional time to service more customers per truck which saves money and allows for greater utilization of each truck and driver. The spray system's operation is under the control of the driver, and he can choose not to spray a bin which the customer has indicated does not require spraying. This again saves money since the spray is applied only to those containers which require it and not to others which may not need to be so treated. This optional spraying also permits modification of only those containers requiring treatment.

The select spray system in accordance with the present invention is easily operated from the cab of the trash collection truck, provides a complete, consistent spray of the container to be sprayed, facilitates a savings in time and money, does not expose the truck driver to the spray being applied, does not require extensive modifications to either the trash container or collection vehicle, and increases customer satisfaction.

BRIEF DESCRIPTION OF THE DRAWINGS

While the novel features of the trash and garbage container select spray system, in accordance with the present invention, are set forth with particularity in the appended claims, a full and complete understanding of the invention may be had by referring to the description of a preferred embodiment as set forth hereinafter, and as may be seen in the accompanying drawings in which:

FIG. 1 is a schematic perspective view showing a front loading trash pickup truck and a trash container generally in accordance with the present invention;

FIG. 2 is a side elevation view, partly in section, and showing the insertion of the spray nozzle of the present invention into the trash container;

FIG. 3 is an elevation view of the trash container in accordance with the present invention and showing the location of the spray nozzle access door; and FIG. 4 is a side elevation view partly in section, showing the spray nozzle and its means for insertion into and retraction out of the trash container.

DESCRIPTION OF A PREFERRED EMBODIMENT

Turning initially to FIG. 1, there may be seen generally at 10 a front loading trash and garbage truck and, at 12, an associated container for use with the select spray system in accordance with the present invention. Truck 10 is generally conventional and is comprised of a cab 14 and a body 16 which carries a receptacle into which the trash or garbage placed in container 12 is dumped. A pair of spaced dumping forks 18 are carried at the front of the truck 10 by a suitable cross bar 20 which extends across the front of truck 10. A pair of spaced hydraulic, or pneumatic, pistons and cylinders 22 are carried on a portion of truck 10's lifting frame generally at 24 and serve to pivot dumping forks 18 about cross bar 20. The dumping forks 18 are insertable through pickup sleeves 26 secured to first and second walls 28 and 30, respectively, of trash or garbage container 12. Container 12 is also provided with a top consisting of one or more hinged covers 32 and may have spaced wheels 34, if desired. It will be understood that the truck 10 and container 12 are well known in the prior art and that the operation of such trucks is also well known. Although not specifically shown, it will be understood that truck 10 is equipped with conventional hydraulic, or pneumatic, pump, controls and reservoirs to allow the truck to function in its known manner to elevate container 12, to rotate the container to empty its contents by gravity into the receptacle portion of truck 10, and to compress the trash or garbage and return the container to the ground. While the truck 10 has hereinabove been described as a front loading refuse truck, it will be obvious to one of skill in the art that the invention is equally applicable to either side or rear loading trash trucks and that although the remaining discussion will be directed to a front loading truck assembly, the invention is not restricted thereto.

Turning again to FIG. 1, it may be seen that cross bar 20 of truck 10 carries a spray nozzle assembly generally at 40. This spray nozzle assembly 40 cooperates with a spray access door 42 provided in a first end wall 44 of trash and/or garbage container 12. Spray nozzle assembly 40 serves to spray a suitable insecticide, deodorant, odor suppressant or other treating material from a source, such as a tank (not shown) carried on the truck 10. It will be understood that the tank from which the insecticide or other material is sprayed is conventional and may be of the type shown in the previously discussed patent to Torrey. A suitable pump may be used to transfer the material from the tank to the spray nozzle assembly. The material to be sprayed into the tank can be either liquid or powder with the type of material and its function being selected by the user. The placement of the supply tank for the insecticide or odor suppressor on the truck and the means for pressurizing this fluid or powder for passage into the container 12 is not part of the present invention and further discussion is deemed unnecessary.

As may be seen in FIG. 4, spray nozzle assembly 40 consists of a spray nozzle 50 carried at a first end of a hollow piston rod 52 with the second end 54 of hollow rod 52 being joined to the supply container (not shown) of the insecticide or odor suppressor by a flexible conduit 56. Piston rod 52 passes through and is secured to a slidable piston or disk 60 which is slidably positioned in an elongated cylinder 62 formed in the body 64 of spray nozzle assembly 40. The ends of cylinder 62 are closed by removable plates 66 which are secured by suitable means such as nuts 68 threaded on studs 70 carried by body 64. Apertures 72 allow passage of piston rod 52 through the end plates and suitable seals (not shown) are provided to insure a tight seal between the piston rod and the plates. As may also be seen in FIG. 4, a pair of fluid ports 74 and 76 are formed at either end of cylinder 62 and are connected to a source of hydraulic or pneumatic pressure by flexible conduits 78 and 80, respectively. Inwardly projecting abutment legs 82 are carried by the plates 66 to limit the travel of piston 60 and hence the travel of piston rod 52. These abutments extend into the cylinder 62 a sufficient distance to limit the travel of piston 60 to the space between the fluid ports 74 and 76. Spray nozzle assembly 40 is secured to cross bar 20 by any suitable means such as welding or by being bolted thereto.

Referring to FIGS. 2 and 3, it may be seen that spray access door 42 is placed in the end wall 44 of the container 12 and with its center at a height "a" above the top surface of the pickup sleeves 26 carried on the side walls 28 and 30 of container 12. Distance "a" is selected to correspond to the distance from the upper surface of the cross bar 20 to nozzle 50 less the thickness of the material used to form the pickup sleeve. In this way, the position of the spray nozzle and the center of the spray access door will always coincide even though the actual size of the containers being used will vary widely. Once the dumping forks 18 have engaged the pickup sleeves 26, the spray nozzle 50 will pass through the access door 42 when it is extended out of cylinder 62 by application of pressure through fluid port 74. The insertion and/or spraying may be implemented at or after initial contact, during the dump cycle or at conclusion of the dump cycle.

Spray access door 42 may be provided with a suitable hinge 84 along its lower interior edge so that door 42 will swing inwardly upon extension of spray nozzle 50 out of cylinder 62, as may be seen in FIG. 2. Spray access door 42 fits in an opening 86 in end wall 44 and is flush therewith in its closed position. The door 42 is hinged along its lower edge to remain closed while the container is being dumped so that trash or garbage will not fall out through opening 86. Instead of hinge 84, other resilient connection means could be provided or door 42 itself could be made of resilient material. Hinge 84 is spring biased to return door 42 to its closed position when spray nozzle 50 is retracted back toward spray nozzle assembly 40 by application of fluid pressure through port 76.

In operation, truck 10 approaches container 12 and the operator inserts the dumping forks 18 into the pickup sleeves 26 of container 12. The operator actuates suitable controls in the cab 14 of truck 10 to elevate container 12 and to dump its contents into the body portion 16 of truck 10. After the contents of container 12 have been emptied into the truck, the operator returns container 12 to its original position. This above-described operation is well known in the art and forms no part of the present invention. Once the container has been emptied and returned to its original position, the operator, after having visually determined that this container is provided with a spray access door 42 and that the customer wants the interior of container 12 treated with an insecticide and/or odor suppressor, actuates suitable controls in the truck cab to apply fluid pressure to port 74 and to vent port 76 thereby causing piston 60 and rod 52 to move to the right, as seen in FIGS. 2 and 4. Spray nozzle 50 is advanced and contacts spray access door 42 to overcome the closing bias of the door and to extend spray nozzle 50 into the interior of container 12. When the spray nozzle is within container 12, the operator actuates other controls to force the insecticide, or whatever material it is desired to spray inside container 12, to flow through the spray nozzle 50. Spraying continues for a specified period of time which may be either manually or automatically controlled by the operator from the cab of the truck. After the spraying has been completed, the spray nozzle 50 is retracted by applying fluid pressure through port 76 and venting pressure through port 74. The spray nozzle is retracted out through spray access door 42 which then closes leaving the trash or garbage container 12 in an empty and sprayed state ready for use by the customer.

The select spray system in accordance with the present invention is suited for use with any conventional trash truck since these vehicles come equipped with suitable hydraulic or pneumatic systems which are easily adapted to operate spray nozzle assembly 40. The lines 78 and 80 to the fluid ports 74 and 76 can be run from the spray nozzle assembly 40 through, for example, cross bar 20 as shown in FIG. 2, where they are protected, to the cab of the vehicle, where they are provided with appropriate control means, and thence to the vehicle's hydraulic or pneumatic system. Similarly, the flexible conduit 56, which supplies the spray material to the nozzle 50 through hollow piston rod 52, may also be run through cross bar 20 for protection and through the vehicle cab to a suitable pressurized supply tank of a conventional nature.

The container 12 to be sprayed can be of any shape or configuration so long as it is capable of being lifted by the dumping forks 18 of the truck 10. While the size of the container can vary, the position of the spray access door will remain a constant which is fixed with respect to the position of the pickup sleeves 26, as was discussed previously. Accordingly, existing containers can be easily modified for use in the select spray system by installing spray access door 42 in the end wall 44 between the pickup sleeves 26 and at a height "a" above the sleeves. The select spray system in accordance with the present invention does not require costly or extensive modifications of either the vehicle or the container and is well suited for use with existing trucks and containers.

While a preferred embodiment of a trash and garbage container select spray system in accordance with the present invention has been hereinabove fully and completely described, it will be obvious to one of skill in the art that a number of changes in, for example, the shape of the container and spray access door, the structure of the body of the spray nozzle assembly, the means for biasing the spray access door, the type of vehicle on which the system is carried and the like could be made without departing from the true spirit and scope of the invention and that the invention is to be limited only by the appended claims.

I claim:

1. A select spray system in combination with a front loading, waste transporting vehicle for spraying a treating material into a waste receiving container, the container being structured to be lifted by and to empty its contents into the cooperating waste transporting vehicle, the spray system comprising:

a spray nozzle assembly for dispensing the treating material into the container, from a supply reservoir carried on the vehicle, said spray nozzle assembly being carried on a front cross bar which extends between a pair of spaced, forwardly extending dumping forks on the vehicle, said spray nozzle assembly being selectively controllable from within the vehicle;

a spray access door in an end wall of the container for affording access to an interior portion of the container, said spray access door being adjacent said spray nozzle assembly when said dumping forks are cooperatively engaging pickup sleeves carried on opposed side walls of the container;

means for selectively inserting a portion of said spray nozzle assembly through said spray access door to spray the treating material into the interior of the container when the container is cooperatively engaged with the vehicle; and means for retracting said portion of said spray nozzle assembly away from the container after spraying is completed whereby the treating material may be sprayed into the container after any waste in the container has been transferred to the vehicle and while the container is still cooperatively engaged with the vehicle.

2. The select spray system of claim 1 wherein said spray access door is biased to a closed position.

3. The select spray system of claim 1 wherein said spray nozzle assembly includes a spray nozzle.

4. The select spray system of claim 3 wherein said spray nozzle is formed as a first end of a hollow piston rod, a second end of said piston rod being connected to the supply reservoir of treating material.

5. The select spray system of claim 4 wherein said piston rod carries a piston intermediate its ends, said piston being slidably carried in a cylinder.

6. The select spray system of claim 5 wherein said cylinder includes fluid ports spaced on either side of said piston and further wherein said fluid ports are joined to a fluid pressure system of the vehicle whereby application of fluid pressure selectively to said ports inserts and retracts said spray nozzle.

* * * * *